(12) United States Patent  
Kelly et al.

(10) Patent No.: US 6,310,066 B1  
(45) Date of Patent: Oct. 30, 2001

(54) ANTIPSYCHOTIC INDOLYL DERIVATIVES

(75) Inventors: Michael G. Kelly, Newbury Park, CA (US); Young H. Kang, Robbinsville, NJ (US)

(73) Assignee: American Home Products Corp., Madison, NJ (US)

( * ) Notice: Subject to any disclaimer, the term of this patent is extended or adjusted under 35 U.S.C. 154(b) by 0 days.

(21) Appl. No.: 09/504,703

(22) Filed: Feb. 16, 2000

Related U.S. Application Data

(63) Continuation-in-part of application No. 09/298,201, filed on Apr. 23, 1999, now abandoned.
(60) Provisional application No. 60/104,596, filed on Apr. 29, 1998.

(51) Int. Cl.[7] .................... A61K 31/496; C07D 403/12; C07D 403/14; C07D 405/14
(52) U.S. Cl. .................. 514/253.06; 514/254.06; 514/254.09; 544/363; 544/370; 544/373
(58) Field of Search ............... 544/370, 373, 544/363; 514/254.06, 254.09, 253.06

(56) References Cited

U.S. PATENT DOCUMENTS

| | | | |
|---|---|---|---|
| 4,335,126 | 6/1982 | Kleemann et al. | 424/250 |
| 4,737,505 | 4/1988 | Guillaume et al. | 514/323 |
| 5,342,845 | 8/1994 | Chokai et al. | 514/305 |
| 5,565,447 | 10/1996 | Forner et al. | 514/212 |
| 5,607,960 | 3/1997 | Wythes | 514/414 |
| 5,607,961 | 3/1997 | Cipollina et al. | 514/415 |
| 5,614,523 | 3/1997 | Audia et al. | 514/252 |
| 5,639,752 | 6/1997 | Macor | 514/245 |
| 5,639,772 | 6/1997 | Hammarberg et al. | 514/374 |
| 5,641,794 | 6/1997 | Booher et al. | 514/364 |
| 5,654,320 | 8/1997 | Catlow et al. | 514/322 |
| 5,654,324 | 8/1997 | Booher et al. | 514/397 |
| 5,670,511 | 9/1997 | Marz et al. | 514/290 |
| 5,693,655 | 12/1997 | Bottcher et al. | 514/323 |
| 5,708,008 | 1/1998 | Audia et al. | 514/323 |
| 5,792,763 | 8/1998 | Fritz et al. | 514/228.2 |

FOREIGN PATENT DOCUMENTS

| | | |
|---|---|---|
| 9748698 | 12/1997 | (WO) . |

OTHER PUBLICATIONS

Rastogi et al., *J. Med. Chem.*, 15 (3), 1972, p. 286–91.
Gueremy et al., J. Med. Chem, 1980, 23, 1306–1310.
Malleron et al., J. Med. Chem., 1993, 36, 1194–1202.
Bergman, J. Heterocyclic Chem., 1970, 1071–1076.
Guillaume et al., Eur. J. Med. Chem., 1987, 22(1), 33–34.
Cheetham et al., Neuropharmacol. 32: 737, 1993.
Cheng and Prusoff, Biochem. Pharmacol., 22, 3099, 1973.
Bowen et al., TINS, vol. 17, No. 4, 1994.
Freter et al., Arzneim.–Forsch. 25 (1), 272–276, 1985.

*Primary Examiner*—Emily Bernhardt
(74) *Attorney, Agent, or Firm*—Joseph M. Mazzarese

(57) ABSTRACT

The present invention provides novel compounds of the general formula:

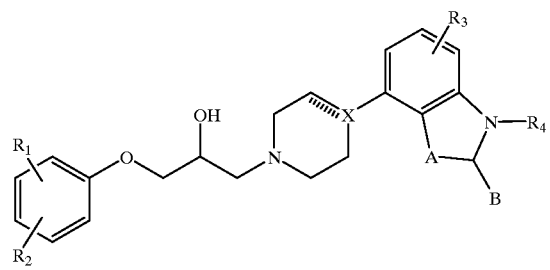

(1)

wherein $R_1$ and $R_2$ are H, OH, F, Cl, Br, I, 1 to 6 carbon alkyl or alkenyl, 1 to 6 carbon alkoxy, aryl, $OR_5$, nitro, amino, $CF_3$ or $R_1$ and $R_2$ are taken together to form a fused ring at the 2,3- or 3,4-positions providing a fused phenyl group or a benzodioxane group, or a 4- or 7-substituted indole group, or a 4- or 5- or 8-substituted quinoline group;

$R_3$ represents a group selected from hydrogen, a 1 to 6 carbon alkyl, a 1 to 4 carbon alkoxy or a halogen;

$R_4$ represents a group selected from hydrogen, 1 to 6 carbon alkyl or $R_5$;

$R_5$ is $CH_2Ph$ in which the phenyl ring can be optionally substituted by a group selected from OMe, halogen, $CF_3$;

X is selected from a group represented by N, $CR_4$, $CHR_4$ and CHCH;

A is selected from a group represented by N, NH, CH and $CH_2$;

B is selected from a group represented by =O, =S, H and H2;

or a pharmaceutically acceptable salt thereof, as well as pharmaceutical compositions and methods of treating central nervous system disorders utilizing these compounds.

16 Claims, No Drawings

ANTIPSYCHOTIC INDOLYL DERIVATIVES

This application is a continuation-in-part of U.S. application Ser. No. 09/298,201, filed Apr. 23, 1999, now abandoned which claims the benefit of U.S. Provisional Application Ser. No. 60/104,59 filed Apr. 29, 1998.

This invention concerns a series of novel β-hydroxy aryloxypropylamines which are effective pharmaceuticals for the treatment of conditions related to or affected by the dopamine D2 receptor and also by the serotonin 1A receptor subtype. The compounds are particularly useful for the treatment of schizophrenia and related psychotic disorders and other conditions such as Parkinson's disease and Alzheimer's disease.

BACKGROUND OF THE INVENTION

In their letter to the editor, TINS, Vol. 17, No. 4, 1994, Bowen et al. note that the cognitive impairment characteristics of Alzheimer's disease may be ameliorated by antagonists at the inhibitory 5-$HT_{1A}$ receeoptor, or by activation of the phospholipase-C-linked cholinergic $M_1$ receptor.

SUMMARY OF THE PRESENT INVENTION

This invention relates to novel indolyl derivatives, to processes for their preparation, to pharmaceutical compositions containing them and to their use in therapy. The compounds are useful for the treatment of psychotic disorders, particularly schizophrenia, by virtue of their ability to antagonize the dopamine D2 receptor. Furthermore, the present invention also provides compounds that are antagonists and agonists at the 5-HT1A receptor subtype and thus compounds of this invention may be used to treat Alzheimer's Disease, Parkinson's Disease, depression and anxiety.

Compounds of the present invention are represented by the general formula (1),

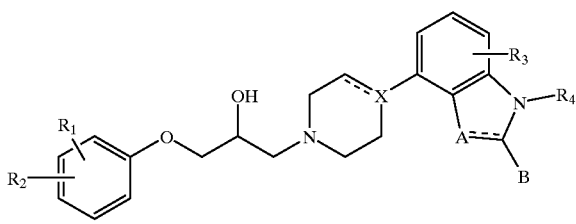

wherein
$R_1$ and $R_2$ are each independently selected from H, OH, F, Cl, Br, I, 1 to 6 carbon alkyl or alkenyl, 1 to 6 carbon alkoxy, aryl, $OR_5$, nitro, amino, $CF_3$ and when $R_1$ and $R_2$ are taken together, form a fused ring at the 2,3- or 3,4-positions providing a fused phenyl group or a benzodioxane group, or a 7-substituted indole group, or a 4- or 5- or 8-substituted quinoline group;

the group formed by the fusion of $R_1$ and $R_2$ being taken together is further optionally substituted by from 1 to 3 groups selected from H, COOH or the $C_1$ to $C_6$ alkyl esters thereof, OH, F, Cl, Br, I, 1 to 6 carbon alkyl or alkenyl, 1 to 6 carbon alkoxy, $OR_5$, —C(O)$NR_6R_7$, nitro, amino, or $CF_3$;

$R_3$ represents a group selected from hydrogen, 1 to 6 carbon alkyl, 1 to 4 carbon alkoxy or halogen;

$R_4$ represents a group selected from hydrogen, 1 to 6 carbon alkyl or $R_5$;

$R_5$ is $CH_2Ph$ in which the phenyl ring can be optionally substituted by a group selected from OMe, halogen, $CF_3$;

$R_6$ and $R_7$ are independently selected from H or $C_1$ to $C_6$ alkyl;

X is selected from a group represented by N, $CR_4$, $CHR_4$ and CHCH;

A is selected from a group represented by N, NH, CH and $CH_2$;

B is selected from a group represented by =O, =S, H and $H_2$;

or A and B may be concatenated together to form indole, benzimidazole, indolone or indoline moieties;

or a pharmaceutically acceptable salt thereof.

It will be understood that the type of substitution indicated by B in the generic groups herein will be controlled by whether A is N, NH, CH or $CH_2$.

The moieties in which A and B may be concatenated together in formula (1) may be represented by the formula:

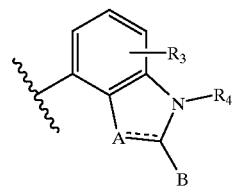

which includes moieties selected from the group of:

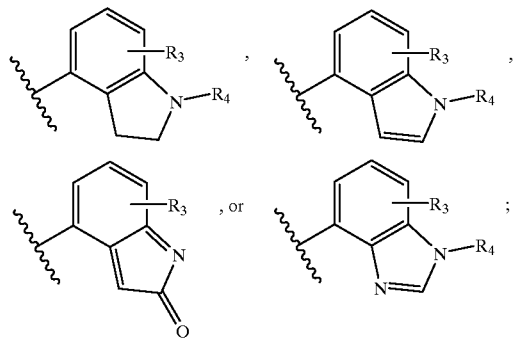

wherein the substituents indicated by $R_3$ and $R_4$ are as defined above.

In the description above, when $R_1$ and $R_2$ are taken together to form a fused phenyl group at the 2,3- or 3,4-positions, the two fused phenyl rings are understood to form a napthyl moiety, optionally substituted by from 1 to 3 groups described above.

The description above states the fusion of $R_1$ and $R_2$ with their corresponding phenyl ring may form a 7-substituted indole group, or a 4- or 5- or 8-substituted quinoline group. In this description, the 4- or 7-positions indicated for the indole group and 5- or 8-positions indicated for the quinoline group indicate the position at which the relevant indole or quinoline moiety is bound to the remainder of the molecule of Formula (1).

The term "aryl" as used in the definitions of $R_1$ and $R_2$ indicates phenyl, benzyl, benzyloxy or pyridine groups, optionally substituted by from 1 to 3 substitutents selected from halogen, $C_1$–$C_6$ alkyl, $C_1$–$C_6$ alkoxy, —S—$C_1$–$C_6$ alkyl, —CN, —OH, —$NO_2$ or —$CF_3$. The most preferred aryl group is phenyl, optionally substituted as just described.

A subset of compounds of this invention includes those of the formula:

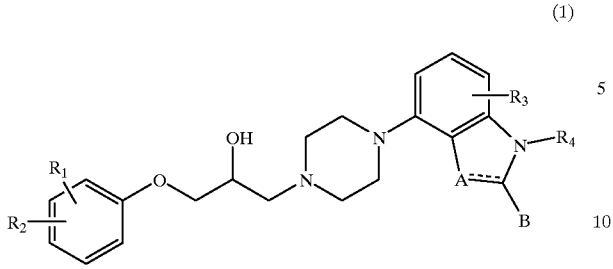

(1)

wherein $R_1$ and $R_2$ are each independently selected from H, OH, F, Cl, Br, I, 1 to 6 carbon alkyl or alkenyl, 1 to 6 carbon alkoxy, $OR_5$, nitro, amino, $CF_3$, phenyl, benzyl, benzyloxy or pyridyl, the aromatic rings of which are optionally substituted by from 1 to 3 substitutents selected from halogen, $C_1$–$C_6$ alkyl, $C_1$–$C_6$ alkoxy, —S—$C_1$—$C_6$ alkyl, —CN, —OH, —$NO_2$ or —$CF_3$;

or $R_1$ and $R_2$ are taken together to form, in conjunction with the phenyl ring to which they are bound, a fused ring at the 2,3- or 3,4-positions providing a fused phenyl group or a benzodioxane group, or a 7-substituted indole group, or a 4- or 5- or 8-substituted quinoline group;

the group formed by the fusion of $R_1$ and $R_2$ being taken together is further optionally substituted by from 1 to 3 groups selected from H, COOH or the $C_1$ to $C_6$ alkyl esters thereof, OH, F, Cl, Br, I, 1 to 6 carbon alkyl, alkenyl or alkoxy, —C(O)$NR_6R_7$, nitro, amino, or $CF_3$;

$R_3$ represents a group selected from hydrogen, a 1 to 6 carbon alkyl, a 1 to 4 carbon alkoxy or a halogen;

$R_4$ represents a group selected from hydrogen, 1 to 6 carbon alkyl or $R_5$;

$R_5$ is $CH_2Ph$ in which the phenyl ring can be optionally substituted by a group selected from OMe, halogen, $CF_3$;

$R_6$ and $R_7$ are independently selected from H or $C_1$ to $C_6$ alkyl;

A is selected from a group represented by N, NH, CH and $CH_2$;

B is selected from a group represented by =O, =S, H and $H_2$;

or A and B may be concatenated together such that the moiety in formula (1) represented by the formula:

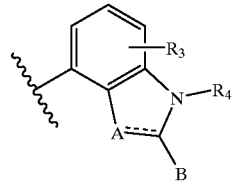

is selected from the group of:

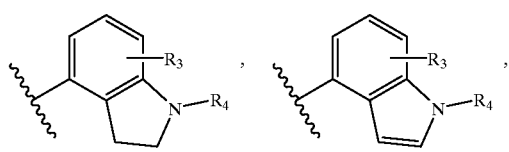

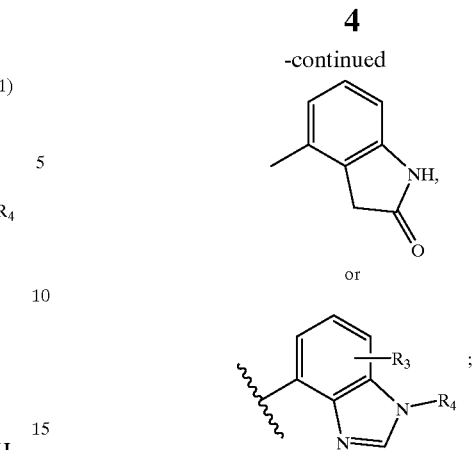

or a pharmaceutically acceptable salt thereof.

The pharmaceutically acceptable salts are the acid addition salts which can be formed from a compound of the above general formula and a pharmaceutically acceptable inorganic acid such as phosphoric, sulfuric, hydrochloric, hydrobromic citric, maleic, fumaric, acetic, lactic or methanesulfonic acid.

DETAILED DESCRIPTION OF THE INVENTION

Compounds of the present invention may be prepared using conventional methods, utilizing for example the disconnections shown in scheme A and scheme B below.

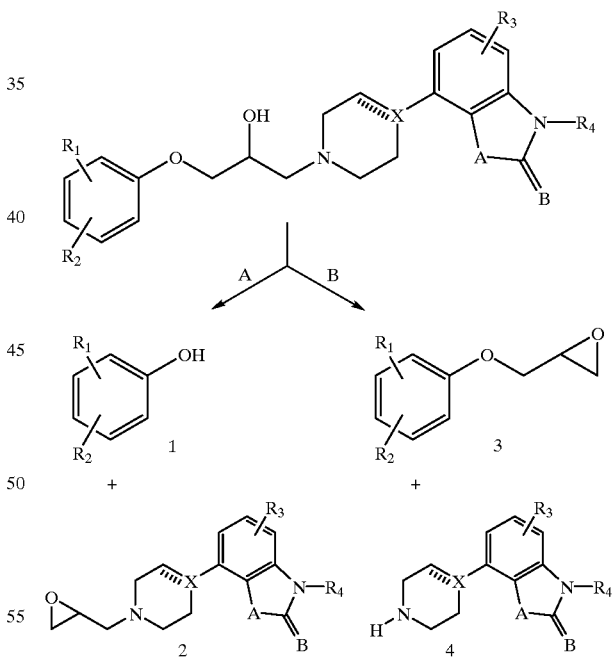

In scheme A, the phenol 1 is reacted with an epoxide of formula 2 to afford the required product. The starting phenol may be commercially available or can be readily obtained by those practiced in the art of organic synthesis. The epoxide 2 is available for example, from the reaction of an amine of formula 4 with optically active or racemic epichlorohydrin or glycidyl tosylate.

In scheme B, the epoxide 3 can be obtained from the reaction of a phenol of formula 1 with optically active or racemic epichlorohydrin or glycidyl tosylate. Reaction of this compound with an amine of formula 4 affords the required product. The product can then be used to form a pharmaceutically acceptable addition salt.

Compounds of the present invention bind with very high to the 5-HT1A receptor and the dopamine D2 receptor and consequently, they are useful for the treatment of central nervous system disorders such as schizophrenia, depression, anxiety, including generalized anxiety, sleep disorders, sexual dysfunction, alcohol and cocaine addiction, and related problems in addition to the treatment of Alzheimer's disease, Parkinson's disease, obesity and migraine. The present compounds can also be used in regimens to increase cognition enhancement. This invention includes methods of treating in mammals each of these maladies, as well as a method of increasing cognition enhancement, the methods comprising administering to a mammal in need thereof an effective amount of one or more of the compounds of this invention, or a pharmaceutically acceptable salt thereof.

It is understood that the therapeutically effective dosage to be used in the treatment of a specific psychosis must be subjectively determined by the attending physician. Variables involved include the specific psychosis or state of anxiety and the size, age and response pattern of the patient. The novel method of the invention for treating conditions related to or are affected by the reuptake of serotonin comprise administering to warm-blooded animals, including humans, an effective amount of at least one compound of this invention or a non-toxic, pharmaceutically acceptable addition salt thereof. The compounds may be administered orally, rectally, parenterally, or topically to the skin and mucosa. The usual daily dose is depending on the specific compound, method of treatment and condition treated. An effective dose of 0.01–1000 mg/Kg may be used for oral application, preferably 0.5–500 mg/Kg, and an effective amount of 0.1–100 mg/Kg may be used for parenteral application, preferably 0.5–50 mg/Kg.

The present invention also includes pharmaceutical compositions containing a compound of this invention, or a pharmaceutically acceptable salt thereof, and one or more pharmaceutically acceptable carriers or excipients.

Applicable solid carriers or excipients can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The affinity of drugs for the dopamine receptor was established by testing the claimed compound's ability to displace [$^3$H]-Spiperone binding in CHO cells stably transfected with the human dopamine D2 receptor. CHO cells expressing the human dopamine D2 receptor were cultured in suspension by expansion (every 3–4 days) in a serum free media to provide approximately $7.5 \times 10^5$ cells/ml. The cells were harvested by centrifugation (900×g for 10 min.), resuspended in half volume of 1×dulbecco PBS solution at pH 7.4, and after a further recentrifugation, the cell pellet was resuspended in 50 mM Tris.HCl (pH 7.4) containing 1.5 mM $CaCl_2$, 5.0 mM EDTA, 5.0 mM KCl, 120 mM NaCl, 1.0 mM PMSF and 1.0 mg % leupeptin. The cells were homogenized, centrifuged at 40,000×g for 30 minutes and resuspended in fresh buffer (10 ml), and the process repeated twice. The final pellet was suspended in a volume of 50.0 mM Tris.HCl sufficient to give a protein concentration of 125.0 $\mu$g/ml of membrane suspension. The binding assay is performed in a 96 well microtiter plate. 100 $\mu$l of buffer is added to the wells, and those receiving a displacer for nonspecific binding (NSB) assessment or test compounds receive 80 $\mu$l of incubation buffer. [3H]-Spiperone (S.A. 89–100 Ci/mmole) is used as ligand and 0.5 nM in 20 $\mu$l volume is added to all wells, followed by the addition of the displacer D-butaclamol (1$\mu$M in 20 $\mu$l) for nonspecific binding determination. The reaction is initiated by the addition of 80 $\mu$l of the tissue membrane, and after 120 minutes at room temperature the wells are harvested using a Brandell® Harvester onto glass fiber filter presoaked in 0.1% polyethylimine. After washing three times with cold 50 mM Tris.HCl, the filter mat is oven dried and sealed in an envelope with melted multitex for scintillation counting in a Wallac 1205 BetaPlate Counter. The data is analyzed and Ki values are computed for active compounds. Using this assay, the following Ki's were determined for a series of standard D2 receptor ligands.

| Compound | D2 binding Ki (nM) |
|---|---|
| Spiperone | 0.08 |
| Clozapine | 28.6 |
| Haloperidol | 0.57 |
| 7-OHDPAT | 96 |
| Sulpiride | 49.4 |

The results for a number of examples of compounds of formula 1 in this standard experimental test procedure were as follows

| Compound | D2 binding Ki (nM) |
|---|---|
| Example 2 | 33.5 |
| Example 5 | 31.9 |
| Example 6 | 10.4 |

High affinity for the serotonin 5-HT$_{1A}$ receptor was established by testing the claimed compound's ability to displace [$^3$H] 8-OH-DPAT binding in CHO cells stably transfected with human 5-HT1A receptor. Stably transfected CHO cells are grown in DMEM containing 10% heat inactivated FBS and non-essential amino acids. Cells are scraped off the plate, transferred to centrifuge tubes, and washed twice by centrifugation (2000 rpm for 10 min., 4° C.) in buffer (50 mM Tris pH 7.5). The resulting pellets are aliquoted and placed at −80° C. On the day of assay, the cells are thawed on ice and resuspended in buffer. The binding assay is performed in a 96 well microtiter plate in a total volume of 250 μL. Non-specific binding is determined in the presence of 10 mM 5HT, final ligand concentration is 1.5 nM. Following a 30 minute incubation at room temperature, the reaction is terminated by the addition of ice cold buffer and rapid filtration through a GF/B filter presoaked for 30 minutes in 0.5% PEI. Compounds are initially tested in a single point assay to determine percent inhibition at 1, 0.1, and 0.01 mM, and Ki values are determined for the active compounds.

| Compound | 5-HT1A binding Ki (nM) |
|---|---|
| Example 1 | 6.0 |
| Example 2 | 7.6 |
| Example 3 | 1.8 |
| Example 4 | 8.8 |
| Example 5 | 12.1 |
| Example 6 | 10.4 |
| Example 7 | 7.2 |
| Example 8 | 4.5 |

The following non-limiting specific examples are included to illustrate the synthetic procedures used for preparing compounds of the formula 1. In these examples, all chemicals and intermediates are either commercially available or can be prepared by standard procedures found in the literature or are known to those skilled in the art of organic synthesis.

EXAMPLE 1

1-(1H-Indol-4yloxy)-3-[4-(1H-indol-4-yl)piperazin-1-yl]-propan-2-ol

A methanolic solution (20 ml) of 1-(indole4-oxy)-2,3-epoxypropane (0.38 g, 2.0 mmole) was added dropwise under a nitrogen atmosphere to a stirred solution of 1-(indol-4-yl)-piperazine (0.4 g, 2.0 mmole) in methanol (75 ml). The mixture was heated to reflux for 2 hrs, concentrated in vacuo, and the product purified by column chromatography over silica gel (CH$_2$Cl$_2$:MeOH 95:5) to afford an oil (0.7 g, 90% yield). Treatment with a 0.25M ethanolic fumaric acid solution gave the required product, which was recrystallized from ethanol to afford the title compound as a white solid. m.p. 147–150° C.

Elemental Analysis for: C23H26N4O2. 1.0C4H4O4 Calculated: C, 64.02; H, 5.97; N, 11.06 Found: C, 64.59; H, 6.36; N, 11.81

EXAMPLE 2

1-(4-Chloro-phenoxy)-3-[4-(1H-indol-4-yl)piperazin-1-yl]-propan-2-ol

A methanolic solution (75 ml) of 4-chlorophenyl-2,3-epoxypropyl ether (0.55 g, 3.0 mmole) and 1-(indol-4yl)-piperazine (0.6 g, 3.0 mmole) was refluxed for 1 hr under an atmosphere of nitrogen. The mixture was concentrated in vacuo, and the product purified by silica gel chromatography (EtOAc:Hexane 90:10) to afford a white solid (1.25 g, 100%). Treatment with a 0.25M ethanolic fumaric acid solution gave the required product, which was recrystallized from ethanol to afford the title compound as a white solid. m.p. 224–2250C.

Elemental Analysis for: C21H24ClN3O2. 0.5C4H4O4 Calculated: C, 62.23; H, 5.9; N, 9.47 Found: C, 61.98; H, 5.79; N, 9.21

EXAMPLE 3

1-[4-(1H-Indol-4-yl)-piperazin-1-yl]-3-(4-methoxy-phenoxy)-propan-2-ol

A methanolic solution (75 ml) of 4-methoxyphenyl-2,3-epoxypropyl ether (0.54 g, 3.0 mmole) and 1-(indol-4-yl)-piperazine (0.6 g, 3.0 mmole) was refluxed for 1 hr under an atmosphere of nitrogen. The mixture was concentrated in vacuo, and the product purified by silica gel chromatography (CH2Cl$_2$:MeOH 90:10) to afford a white solid (1.1 g, 96%). Treatment with a 0.25M ethanolic fumaric acid solution gave the required product, which was recrystallized from ethanol to afford the title compound as a white solid. m.p. 226–227° C.

Elemental Analysis for: C22H27N3O3. 0.5C4H4O4 Calculated: C, 65.59; H, 6.65; N, 9.56 Found: C, 65.36; H, 6.48; N, 9.36

EXAMPLE 4

1-[4-(1H-Indol-4-yl)-piperazin-1-yl]-3-(4-nitro-phenoxy)-propan-2-ol

A methanolic solution (65 ml) of 1,2-epoxy-3-(4-nitrophenoxy)-propane (0.59 g, 3.0 mmole) and 1-(indol-4yl)-piperazine (0.6 g, 3.0 mmole) was refluxed for 1 hr under an atmosphere of nitrogen. The mixture was concentrated in vacuo to afford the product as a yellow solid (1.1 g, 93%). Treatment with a 4M etheral HCl solution gave the required product, which was recrystallized from ethanol to afford the title compound as a light yellow solid. m.p. 248° C.

Elemental Analysis for: C21H24N4O4. 1.0HCl Calculated: C, 58.26; H, 5.82; N, 12.94 Found: C, 57.92; H, 5.76; N, 12.66

EXAMPLE 5

1-(2-Chloro-phenoxy)-3-[4-(1H-indol-4-yl) piperazin-1-yl]-propan-2-ol

A methanolic solution (75 ml) of 1-(2-chlorophenoxy)-2, 3-epoxypropane (0.55 g, 3.0 mmole) and 1-(indol-4-yl)-piperazine (0.6 g, 3.0 mmole) was refluxed for 1 hr under an atmosphere of nitrogen. The mixture was concentrated in vacuo, and the product purified by silica gel chromatography ($CH_2Cl_2$:MeOH 90:10) to afford a white solid (1.09 g, 94%). Treatment with a 0.25M ethanolic fumaric acid solution gave the required product, which was recrystallized from ethanol to afford the title compound as a white solid. m.p. 207° C.

Elemental Analysis for: C21H24ClN3O2. 0.5C4H4O4 Calculated: C, 62.23; H, 5.9; N, 9.47 Found: C, 62.13; H, 5.72; N, 9.34

EXAMPLE 6

1-(4-Fluoro-phenoxy)-3-[4-(1H-indol-4-yl) piperazin-1-yl]-propan-2-ol

A methanolic solution (50 ml) of 1-(4-fluorophenoxy)-2, 3-epoxypropane (0.50 g, 3.0 mmole) and 1-(indol-4yl)-piperazine (0.6 g, 3.0 mmole) was refluxed for 1 hr under an atmosphere of nitrogen. The mixture was concentrated in vacuo, and the product purified by silica gel chromatography (EtOAc) to afford a white solid (1.1 g, 99%). Treatment with a 0.25M ethanolic fumaric acid solution gave the required salt, which was recrystallized from ethanol to afford the title compound as a white solid. m.p. 234–235° C.

Elemental Analysis for: C21H24FN3O2. 0.5C4H4O4 Calculated: C, 64.62; H, 6.13; N, 9.83 Found: C, 64.38; H, 6.01; N, 9.67

EXAMPLE 7

4-{2-Hydroxy-3-[4(1H-indol-4-yl)-piperazin-1-yl] propxy}-1H-indole-2-carboxylic acid amide A methanolic solution (50 ml) of 1-(2-carboxamidoindol-4-oxy)-2,3-epoxypropane (0.83 g, 1.5 mmole) and 1-(indol-4-yl)-piperazine (0.6 g, 3.0 mmole) was refluxed for 0.5 hr under an atmosphere of nitrogen. The mixture was concentrated in vacuo, and the product purified by silica gel chromatography ($CH_2Cl_2$:MeOH 90:10) to afford a white solid (1.24 g, 97%). Treatment with a 1.0M etheral HCl solution gave the required product, which was recrystallized from ethanol to afford the title compound as a white solid. m.p. 258–259° C.

Elemental Analysis for: C24H27N5O3. 1.0HCl Calculated: C, 60.5; H, 6.08; N, 14.7 Found: C, 60.31; H, 5.89; N, 14.6

EXAMPLE 8

1-(Biphgenyl-2-yloxy)-3-[4-(1H-indol-4-yl) piperazin-1-yl]-propan-2-ol

A methanolic solution (50 ml) of 2-biphenyiglycidyl ether (0.68 g, 1.5 mmole) and 1-(indol-4yl)-piperazine (0.6 g, 3.0 mmole) was refluxed for 15 hrs under an atmosphere of nitrogen. The mixture was concentrated in vacuo, and the product purified by silica gel chromatography (EtOAc) to afford a white solid (1.23 g, 96%). Treatment with a 0.25M ethanolic fumaric acid solution gave the required salt, which was recrystallized from ethanol to afford the title compound as a white solid. m.p. 214–215° C.

Elemental Analysis for: C27H29N3O2. 1.0C4H4O4 Calculated: C, 68.49; H, 6.12; N, 7.73 Found: C, 68.6; H, 6.12; N, 7.88

EXAMPLE 9

1-(1H-Indol-4-yloxy-3-[4-(1H-henzimidazole-4-yl) piperazin-1-yl]-propan-2-ol The title compound is prepared from the reaction of 1-(indole-4-oxy)-2,3-epoxypropane (2.0 mmole) and 1-(1H-henzimidazole-4-yl)piperazine (2 mmole) according to the above procedures.

EXAMPLE 10

1-(1H-Indol-4-yloxy)-3-[4-(1H-2,3-dihydroindol-4-yl)piperazin-1-1yl]-propan-2-ol The title compound is prepared from the reaction of 1-(indole-4-oxy)-2,3-epoxypropane (2.0 mmole) and 1-(1H-2,3-dihydroindol-4-yl)piperazine (2 mmole) using the procedures outlined in the previous examples.

EXAMPLE 11

1-(1H-Indol-4-yloxy)-3-[4-(1H-2-oxo-indol-4-yl) piperazin-1-yl]-propan-2-ol

The title compound is prepared from the reaction of 1-(indole-4-oxy)-2,3-epoxypropane (2.0 mmole) and 1-(1H-2-oxindol-4-yl)piperazine (2 mmole) using the procedures outlined in the previous examples.

$^3$H-Paroxetine binding to assess affinity of drugs for the serotonin transporter:

A protocol similar to that used by Cheetham et al. (Neuropharmacol. 32:737, 1993) was used to determine the affinity of compounds for the serotonin transporter. Briefly, frontal cortical membranes prepared from male S.D. rats were incubated with $^3$H-paroxetine (0.1 nM) for 60 min at 25° C. All tubes also contained either vehicle, test compound (one to eight concentrations), or a saturating concentration of fluoxetine (10 $\mu$M to define specific binding. All reactions are terminated by the addition of ice cold Tris buffer followed by rapid filtration using a Tom Tech filtration device to separate bound from free $^3$H-paroxetine. Bound radioactivity was quantitated using a Wallac 1205 Beta Plate® counter. Results achieved are expressed below as % inhibition of Paroxetine binding at a given concentration.

| Compound | SSRi % Inhibition (rat brain) at 0.1 $\mu$M |
| --- | --- |
| Example 1 | 32% |
| Example 2 | 13% |
| Example 3 | 17% |
| Example 4 | 15% |
| Example 5 | 11% |
| Example 6 | 0% |
| Example 7 | 3% |
| Example 8 | 0% |

We claim:
1. A compound according to the formula:

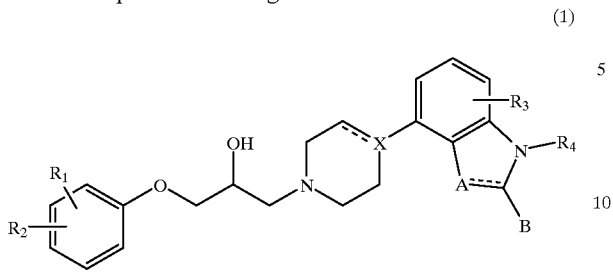
(1)

wherein

R₁ and R₂ are each independently selected from H, OH, F, Cl, Br, I, 1 to 6 carbon alkyl or alkenyl, 1 to 6 carbon alkoxy, aryl, OR₅, nitro, amino, CF₃ and when R₁ and R₂ are taken together, form a fused ring at the 2,3- or 3,4- positions providing a fused phenyl group or a benzodioxane group, or a 4- or 7-substituted indole group, or a 5- or 8-substituted quinoline group;

the group formed by the fusion of R₁ and R₂ being taken together is further optionally substituted by from 1 to 3 groups selected from H, COOH or the C₁ to C₆ alkyl esters thereof, OH, F, Cl, Br, I, 1 to 6 carbon alkyl or alkenyl, 1 to 6 carbon alkoxy, OR₅, —C(O)NR₆R₇, nitro, amino, or CF₃;

R₃ represents a group selected from hydrogen, a 1 to 6 carbon alkyl, a 1 to 4 carbon alkoxy or a halogen;

R₄ represents a group selected from hydrogen, 1 to 6 carbon alkyl or R₅;

R₅ is CH₂Ph in which the phenyl ring can be optionally substituted by a group selected from OMe, halogen, CF₃;

R₆ and R₇ are independently selected from H or C₁ to C₆ alkyl;

X is N;

A is selected from a group represented by N, CH and CH₂; and

B is selected from a group represented by =O, H and H₂; such that the moiety in formula (1) represented by the formula:

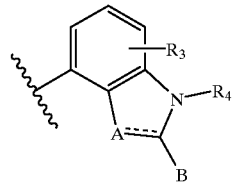

is selected from the group of:

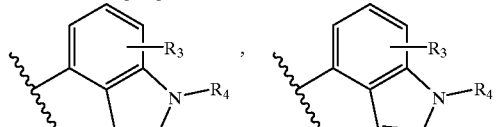

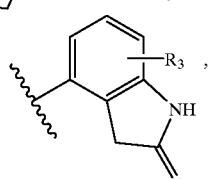

or

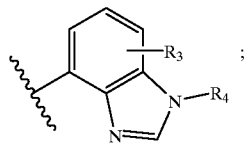

with the proviso that when R₁ and R₂ taken together with the ring to which they are attached form a 4- or 7-substituted indole group, then B is =O;

or a pharmaceutically acceptable salt thereof.

2. A compound according to claim 1 of the formula:

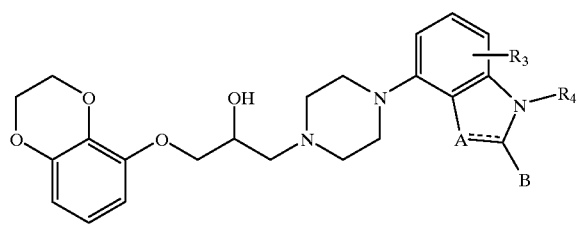

or

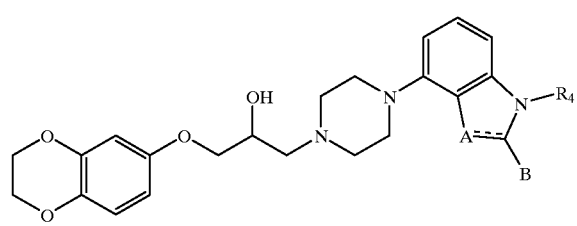

wherein:

the moiety represented by the formula:

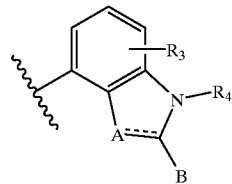

is selected from the group of:

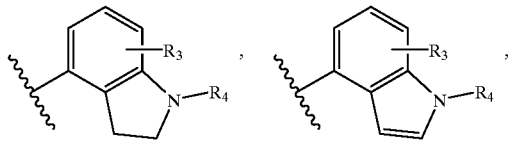

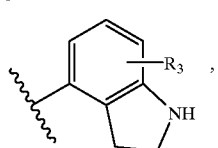

or

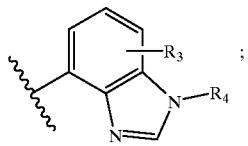

R₃ is selected from hydrogen, 1 to 6 carbon alkyl, 1 to 4 carbon alkoxy or halogen;

$R_4$ represents a group selected from hydrogen, 1 to 6 carbon alkyl 1 to 4 carbon alkoxy or halogen;

the benzodioxane group is optionally substituted by from 1 to 3 groups selected from H, COOH or the $C_1$ to $C_6$ alkyl esters thereof, OH, F, Cl, Br, I, 1 to 6 carbon alkyl, alkenyl or alkoxy, —C(O)NRA, nitro, amino, or $CF_3$; and $R_6$ and $R_7$ are independently selected from H or C, to $C_6$ alkyl; or a pharmaceutically acceptable salt thereof.

3. A compound according to claim 1 of the formula:

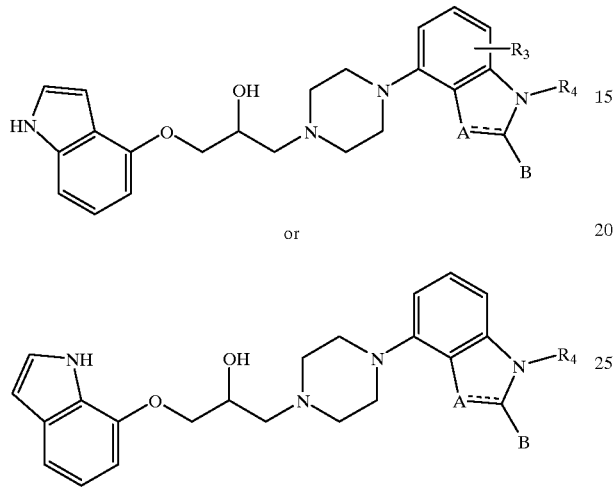

or

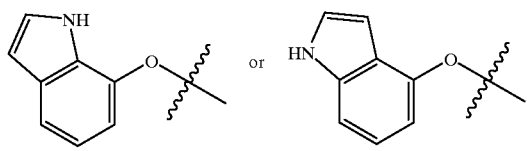

wherein:
the moiety represented by the formula:

is

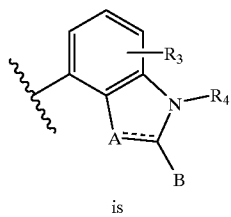

;

$R_3$ is selected from hydrogen, 1 to 6 carbon alkyl, 1 to 4 carbon alkoxy or halogen;

$R_4$ represents a group selected from hydrogen, 1 to 6 carbon alkyl 1 to 4 carbon alkoxy or halogen;

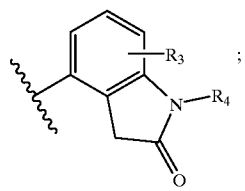

the indole group is optionally substituted by from 1 to 3 groups selected from H, COOH or the $C_1$ to $C_6$ alkyl esters thereof, OH, F, Cl, Br, I, 1 to 6 carbon alkyl, alkenyl or alkoxy, —C(O)NR$_6$R$_7$, nitro, amino, or $CF_3$; and $R_6$ and $R_7$ are independently selected from H or $C_1$ to $C_6$ alkyl; or a pharmaceutically acceptable salt thereof.

4. A compound according to claim 1 of the formula:

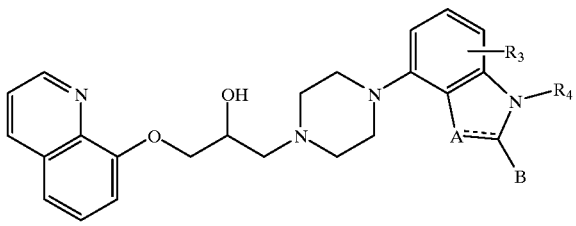

or

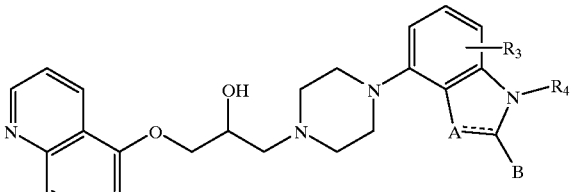

wherein:
the moiety represented by the formula:

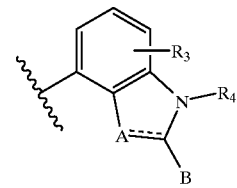

is selected from the group of:

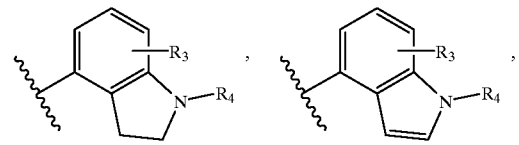

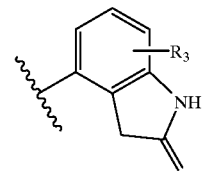

or

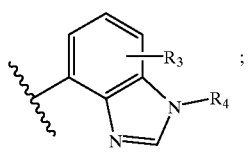

;

$R_3$ is selected from hydrogen, 1 to 6 carbon alkyl, 1 to 4 carbon alkoxy or halogen;

$R_4$ represents a group selected from hydrogen, 1 to 6 carbon alkyl 1 to 4 carbon alkoxy or halogen;

the quinoline group is optionally substituted by from 1 to 3 groups selected from H, COOH or the $C_1$ to $C_6$ alkyl esters thereof, OH, F, Cl, Br, I, 1 to 6 carbon alkyl, alkenyl or alkoxy, —C(O)NR$_6$A, nitro, amino, or $CF_3$; and $R_6$ and $R_7$ are independently selected from H or $C_1$ to $C_6$ alkyl; or a pharmaceutically acceptable salt thereof.

5. A compound of claim 1 which is 1-(4-chloro-phenoxy)-3-[4-(1H-indol-4-yl)-piperazin-1-yl]-propan-2-ol or a pharmaceutically acceptable salt thereof.

6. A compound of claim 1 which is 1-[4-(1H-indol-4-yl)-piperazin-1-yl]-3-(4-methoxy-phenoxy)-propan-2-ol.

7. A compound of claim 1 which is 1-[4-(1H-indol-4-yl)-piperazin-1-yl]-3-(4-nitro-phenoxy)-propan-2-ol or a pharmaceutically acceptable salt thereof.

8. A compound of claim 1 which is 1-(2-chloro-phenoxy)-3-[4-(1H-indol-4-yl)-piperazin-1-yl]-propan-2-ol or a pharmaceutically acceptable salt thereof.

9. A compound of claim 1 which is 1-(4-fluoro-phenoxy)-3-[4-(1H-indol-4-yl)-piperazin-1-yl]-propan-2-ol or a pharmaceutically acceptable salt thereof.

10. A compound of claim 1 which is 4-{2-hydroxy-3-[4-(1H-indol-4-yl)-piperazin-1-yl]propoxy}-1H-indole-2-carboxylic acid amide or a pharmaceutically acceptable salt thereof.

11. A compound of claim 1 which is 1-(biphenyl-2-yloxy)-3-[4-(1H-indol-4-yl)-piperazin-1-yl]-propan-2-ol or a pharmaceutically acceptable salt thereof.

12. A compound of claim 1 which is 1-(1H-Indol-4-yloxy)-3-[4-(1H-benzimidazole-4-yl)piperazin-1-yl]-propan-2-ol or a pharmaceutically acceptable salt thereof.

13. A compound of claim 1 which is 1-(1H-Indol-4-yloxy)-3-[4-(1H-2,3-dihydroindol-4-yl) piperazin-1-yl]-propan-2-ol or a pharmaceutically acceptable salt thereof.

14. A compound of claim 1 which is 1-(1H-Indol4-yloxy)-3-[4-(1H-2-oxo-indol-4-yl) piperazin-1-yl]-propan-2-ol or a pharmaceutically acceptable salt thereof.

15. A pharmaceutical composition comprising a therapeutically effective amount of a compound according to the formula:

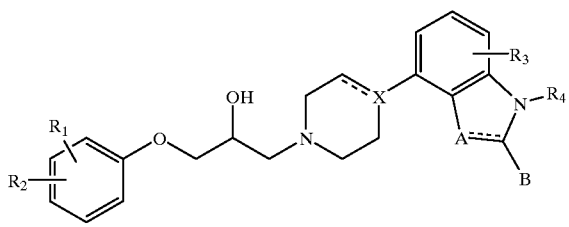

wherein
$R_1$ and $R_2$ are each independently selected from H, OH, F, Cl, Br, I, 1 to 6 carbon alkyl or alkenyl, 1 to 6 carbon alkoxy, aryl, $OR_5$, nitro, amino, $CF_3$ and when $R_1$ and $R_2$ are taken together, form a fused ring at the 2,3- or 3,4- positions providing a fused phenyl group or a benzodioxane group, or a 4- or 7-substituted indole group, or a 5- or 8-substituted quinoline group;

the group formed by the fusion of $R_1$ and $R_2$ being taken together is further optionally substituted by from 1 to 3 groups selected from H, COOH or the $C_1$ to $C_6$ alkyl esters thereof, OH, F, Cl, Br, I, 1 to 6 carbon alkyl or alkenyl, 1 to 6 carbon alkoxy, $OR_5$, —$C(O)NR_6R_7$, nitro, amino, or $CF_3$;

$R_3$ represents a group selected from hydrogen, a 1 to 6 carbon alkyl, a 1 to 4 carbon alkoxy or a halogen;

$R_4$ represents a group selected from hydrogen, 1 to 6 carbon alkyl or $R_5$;

$R_5$ is $CH_2Ph$ in which the phenyl ring can be optionally substituted by a group selected from OMe, halogen, $CF_3$;

$R_6$ and $R_7$ are independently selected from H or $C_1$ to $C_6$ alkyl;

X is N;
A is selected from a group represented by N, CH and $CH_2$; and
B is selected from a group represented by =O, H and $H_2$; such that the moiety in formula (1) represented by the formula:

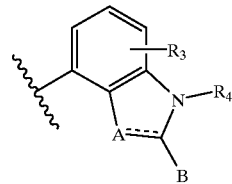

is selected from the group of:

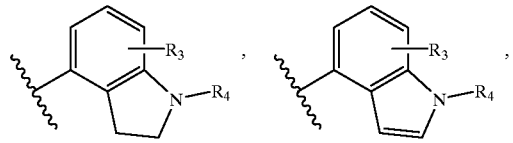

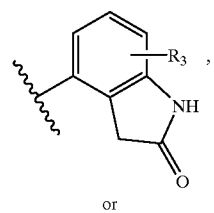

or

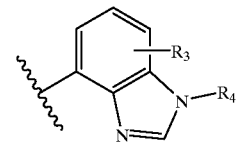

with the proviso that when $R_1$ and $R_2$ taken together with the ring to which they are attached form a 4- or 7-substituted indole group, then B is =O;

or a pharmaceutically acceptable salt thereof, and a pharmaceutically acceptable carrier or excipient.

16. A method of treating a patient suffering from schizophrenia, comprising providing to a patient in need thereof, a therapeutically effective amount of a compound according to the formula:

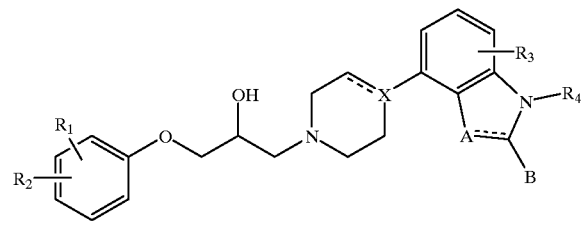

(1)

wherein
$R_1$ and $R_2$ are each independently selected from H, OH, F, Cl, Br, I, 1 to 6 carbon alkyl or alkenyl, 1 to 6 carbon alkoxy, aryl, $OR_5$, nitro, amino, $CF_3$ and when $R_1$ and $R_2$ are taken together, form a fused ring at the 2,3- or 3,4- positions providing a fused phenyl group or a benzodioxane group, or a 4- or 7-substituted indole group, or a 5- or 8-substituted quinoline group;

the group formed by the fusion of $R_1$ and $R_2$ being taken together is further optionally substituted by from 1 to 3 groups selected from H, COOH or the $C_1$ to $C_6$ alkyl esters thereof, OH, F, Cl, Br, I, 1 to 6 carbon alkyl or alkenyl, 1 to 6 carbon alkoxy, $OR_5$, —$C(O)NR_6R_7$, nitro, amino, or $CF_3$;

$R_3$ represents a group selected from hydrogen, a 1 to 6 carbon alkyl, a 1 to 4 carbon alkoxy or a halogen;

$R_4$ represents a group selected from hydrogen, 1 to 6 carbon alkyl or $R_5$;

$R_5$ is $CH_2Ph$ in which the phenyl ring can be optionally substituted by a group selected from OMe, halogen, $CF_3$;

$R_6$ and $R_7$ are independently selected from H or $C_1$ to $C_6$ alkyl;

X is N;

A is selected from a group represented by N, CH and $CH_2$; and

B is selected from a group represented by =O, H and $H_2$; such that the moiety in formula (1) represented by the formula:

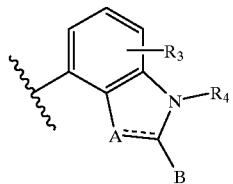

is selected from the group of:

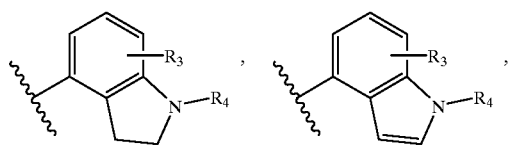

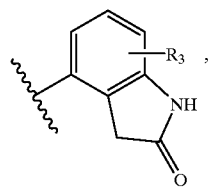

or

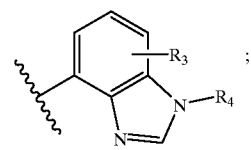

with the proviso that when $R_1$ and $R_2$ taken together with the ring to which they are attached form a 4- or 7-substituted indole group, then B is =O; or a pharmaceutically acceptable salt thereof.

* * * * *